US011229573B2

United States Patent
Rakshit et al.

(10) Patent No.: US 11,229,573 B2
(45) Date of Patent: Jan. 25, 2022

(54) SEXUAL STIMULATION DEVICE

(71) Applicant: Mysteryvibe Limited, Buckinghamshire (GB)

(72) Inventors: Soumyadip Rakshit, Buckinghamshire (GB); Robert Paul Weekly, Buckinghamshire (GB); Shanshan Xu, Buckinghamshire (GB); Stephanie Barraclough, Buckinghamshire (GB)

(73) Assignee: Mysteryvibe Limited, Hounslow (GB)

( * ) Notice: Subject to any disclaimer, the term of this patent is extended or adjusted under 35 U.S.C. 154(b) by 0 days.

(21) Appl. No.: 16/958,184

(22) PCT Filed: Jan. 2, 2019

(86) PCT No.: PCT/GB2019/050003
§ 371 (c)(1),
(2) Date: Jun. 26, 2020

(87) PCT Pub. No.: WO2019/135072
PCT Pub. Date: Jul. 11, 2019

(65) Prior Publication Data
US 2020/0368103 A1 Nov. 26, 2020

(30) Foreign Application Priority Data
Jan. 2, 2018 (GB) ..................... 1800029

(51) Int. Cl.
*A61H 19/00* (2006.01)

(52) U.S. Cl.
CPC ............. *A61H 19/32* (2013.01); *A61H 19/34* (2013.01); *A61H 19/50* (2013.01)

(58) Field of Classification Search
CPC ...... A61F 5/41; A61F 5/451; A61F 2005/411; A61F 2005/414; A61F 2005/417;
(Continued)

(56) References Cited

U.S. PATENT DOCUMENTS

| 3,633,572 | A | | 1/1972 | Wiggins |
| 5,439,007 | A | * | 8/1995 | Fischer ................. A61F 5/41 |
| | | | | 128/842 |

(Continued)

FOREIGN PATENT DOCUMENTS

| GB | 2540746 A | 2/2017 |
| WO | 2015054436 A1 | 4/2015 |

OTHER PUBLICATIONS

International Search Report and Written Opinion of the International Searching Authority Application No. PCT/GB2019/050003 dated Apr. 12, 2019 19 pages.
(Continued)

*Primary Examiner* — Samuel G Gilbert
(74) *Attorney, Agent, or Firm* — Wesley Whitmyer

(57) ABSTRACT

A sexual stimulation device has a loop through which a user can insert their penis. A perineum stimulating portion is configured to contact the user's perineum during use, and a deformable connector extends between the loop and the perineum stimulating portion. The deformable connector is deformable between a first shape and a second shape, and is biased towards the first shape such that the loop and the perineum stimulating portion are biased towards the user's body during use.

17 Claims, 6 Drawing Sheets

(58) Field of Classification Search
CPC ........ A61H 19/00; A61H 19/30; A61H 19/32; A61H 19/34; A61H 19/50; A61H 2201/1647; A61H 2201/1645; A61H 2201/165; A61H 2201/1652
See application file for complete search history.

(56) References Cited

U.S. PATENT DOCUMENTS

| | | | | |
|---|---|---|---|---|
| 2008/0065187 | A1* | 3/2008 | Squicciarini | A61F 2/26 607/143 |
| 2010/0076257 | A1* | 3/2010 | DeAlva | A61H 19/34 600/38 |
| 2015/0174001 | A1* | 6/2015 | Milton | A61H 19/34 600/41 |
| 2017/0360653 | A1* | 12/2017 | Marshall | A61H 39/04 |

OTHER PUBLICATIONS

International Search Report Application No. GB1800029.9 dated May 24, 2018 4 pages.

\* cited by examiner

SEXUAL STIMULATION DEVICE

TECHNICAL FIELD

The present teaching lies in the field of sexual enhancement devices, in particular devices used to promote and maintain a user's erection.

BACKGROUND

Known sexual enhancement devices for men include penis rings. These devices include several limitations. Some devices have been provided in fixed sizes which are not suitable for all users. Furthermore, these fixed size penis rings are typically not capable of accommodating the growth in a user's penis when the user's penis is erect. There is therefore a need to provide a penis ring which is adaptable in size.

There is also the problem that known penis rings fail to provide adequate stimulation to the user, especially during intercourse, and as such do not actively promote blood flow to the user's penis. Providing such stimulation requires overcoming a number of different problems, as will be explained in relation to the different aspects of the present teaching.

SUMMARY

The present teaching has several different aspects each providing a benefit. The benefits of the different aspects are synergistic, and any embodiment of a given aspect of the present teaching may be combined with any other embodiment of that aspect or with any embodiments of a different aspect of the present teaching.

According to a first aspect of the present teaching there is provided a sexual stimulation device comprising: a loop through which a user can insert their penis; a perineum stimulating portion configured to contact the user's perineum during use; and a deformable connector extending between the loop and the perineum stimulating portion, wherein the deformable connector is deformable between a first shape and a second shape, and wherein the deformable connector is biased towards the first shape such that the loop and the perineum stimulating portion are biased towards the user's body during use In this way, the deformable connector can be deflected from its equilibrium position when it is fitted onto a user. The deflection of the deformable connector can generate a biasing force when the ring is at the base of the user's penis which presses the perineum stimulating portion against a user's perineum and ensures the ring is held at the base of the user's penis. This can allow the device to be worn securely by users. The flexibility of the connector also means that the device can be worn by users with different body shapes. The secure fit of the device in use means that the loop and the perineum stimulator are urged into the user's body. This can allow the effect of any vibrations to be focused on the penis and the perineum which can actively promote blood flow to a user's penis, helping to promote and maintain an erection. The device can be held securely in position during intercourse without any straps or other components that might cause discomfort. A closed or open loop may be provided in different embodiments through which the user can insert their penis.

According to a second aspect of the present teaching there is provided a sexual stimulation device comprising: a loop through which a user can insert their penis, the loop comprising one or more vibrators; a perineum stimulating portion comprising control circuitry; and a connector extending between the loop and the perineum stimulating portion; wherein the control circuitry in the perineum stimulating portion is acoustically isolated from vibrations in the loop by means of the connector.

In this way, the circuit board controlling the one or more vibrators which induce said vibrations may be effectively isolated from vibrations that could cause damage. This also acts to localize the vibrations to the loop and connector, thereby improving the efficiency of the vibrators in these regions.

According to a third aspect of the present teaching there is provided a loop through which a user can insert their penis; a perineum stimulating portion comprising a housing and a cavity in which is provided an insert; a first vibrator connected to the insert; and a connector extending between the loop and the perineum stimulating portion; wherein the housing of the perineum stimulating portion is acoustically isolated from the vibrations of the vibrator by means of the insert.

In this way, the insert can vibrate relative to the housing of the perineum stimulating portion. This means that a rigid perineum stimulating portion can be provided with a floating insert that can maximize transfer of vibrations from the vibrator to the user's perineum. Control circuitry may be provided within the housing, and by providing the vibrator in the insert this control circuitry may be protected and isolated from vibrator vibrations that could otherwise cause damage and sever electrical connections, especially solder connections. The cavity in the housing is preferably a through-hole so that the insert can be provided entirely within the housing. Preferably the insert is sized and shaped so that its outer surface matches with the outer surface of the housing and, together, they provide a continuous outer surface for the perineum stimulating portion.

The insert preferably comprises a first material and the perineum stimulating portion preferably comprises a second material, the second material being more rigid than the first material. This causes the vibrations to be localized to the insert itself, and the likelihood of damage to the circuit board is thereby reduced. However, it is not necessary for the insert to be less rigid than the perineum stimulating portion in order to localize vibrations in the insert to an extent sufficient to prevent damage to the circuit board. In some embodiments the interface between the insert and the perineum stimulating portion may dissipate the energy of vibrations the insert. Preferably the interface allows relative movement between the housing and the insert, while still providing a secure connection. For example, the interface may provide a soft and flexible material that can act as an acoustic dampener. One suitable material for use at the interface may be silicone, but others would occur to a skilled person.

The second material preferably has a larger Young's modulus than the first material in the insert. However, the relative rigidity of the perineum stimulating portion compared with the insert may be configured by altering their respective geometries.

According to a fourth aspect of the present teaching there is provided a sexual stimulation device comprising: a perineum stimulating portion configured to contact the user's perineum during use, the perineum stimulating portion comprising one or more vibrators configured to stimulate the user's perineum; a loop through which a user can insert their penis, wherein the loop includes one or more vibrators that are positioned adjacent the ventral side of the user's penis in order to stimulate the ventral side of the user's penis; and a connector extending between the loop and the perineum stimulating portion.

It has been determined that stimulation of the ventral side of the user's penis together with stimulation of the perineum can advantageously provoke blood flow and maintain a user's erection. Vibrators are provided in the loop at a position that can provide the necessary stimulation. The device can be worn by a user during intercourse in order to promote maintenance of an erection.

According to a fifth aspect of the present teaching, there is provided a sexual stimulation device comprising: an open loop through which a user can insert their penis, the open loop having a first end and a second end and being movable from a first configuration in which the first end is a first distance from the second end to a second configuration in which the first end is a second distance from the second end, the second distance being greater than the first distance; a perineum stimulating portion configured to contact the user's perineum during use; and a connector extending between the loop and the perineum stimulating portion.

In this way, the open loop can adapt to different sizes of penis and can also grow in diameter when user has an erection. A resilient inner core may be provided in the loop to bias the ring towards its equilibrium shape, thereby putting pressure on the user's penis, while a deformable outer covering may be provided to provide some cushioning and prevent pain during use.

The open ring may also be moveable to a third configuration in which the first end is a third distance from the second end, the third distance being smaller than the first distance. This allows the open ring to be tightened to increase the pressure on a user's penis.

The device may comprise a first string connected to the first end of the open loop; a second string connected to the second end of the open loop; and a toggle engaging the first and second strings. The toggle may be moveable relative to the first and second strings and may be lockable in position relative to the first and second strings in order to urge the open loop towards the third configuration.

The deformable connector preferably comprises a resilient first material that biases the deformable connector towards the first shape. In this way, the deformable connector can act as a material spring which is biased towards the first shape. In some embodiments the deformable connector may have a distinct inner part, and various different materials may be used to provide an outer covering, preferably such that the outer covering is flexible and deformable.

It is preferable that the perineum stimulating portion is not deformable, or is at least less deformable than the connector, such that deformations of the device do not result in significant deformation of the perineum stimulating portion. As such, in preferred embodiments the perineum stimulating portion comprises a second material, such that the perineum stimulating portion is more rigid than the deformable connector.

In order to better accommodate a user, the deformable connector preferably comprises a pair of arms with a gap between them in which a user's testicles can be received. In alternative embodiments, the deformable connector is configured such as to be positioned around the user's testicles during use of the device.

In order to improve the comfort of the user, the sexual stimulation device preferably comprises a deformable outer covering. This need not cover the entirety of the device. For example, the outer covering preferably does not cover the insert so that it can be removed from the cavity of the perineum stimulating portion.

The connector preferably acts to dissipate the energy of vibrations. In order to increase the dissipative effect, the connector preferably comprises a first material while the perineum stimulating portion preferably comprises a second material, the second material being more rigid than the first material. The vibrations will therefore be dissipated mainly in the more flexible connector, and tend to have less effect on the relatively rigid perineum stimulating portion. The second material will typically have a larger Young's modulus than the first material, but the perineum stimulating portion could also be made more rigid than the connector by suitably configuring the respective geometries of the connector and the perineum stimulating portion.

The loop is preferably also comprised of the first material, such that the loop and the connector may be manufactured as a single unit, but it is also possible for the loop to be separate from the connector. For example, the loop could be formed from an outer covering provided over the connector.

Certain manufacturing complications may arise when joining the connector to the perineum stimulating portion, especially when the connector comprises a different material to the perineum stimulating portion. In order to overcome these complications, the perineum stimulating portion preferably comprises two or more parts configured to hold the connector in a clamped arrangement. This allows the connector to be manufactured separately from the perineum stimulating portion, and ensures that the connector is securely fastened to the perineum stimulating portion.

The connector may comprise one or more vibrators positioned adjacent a user's testicles, in use, in order to stimulate the user's testicles, and in embodiments where the connector is configured to receive said user's testicles it is typical to provide the one or more vibrators such that they will be positioned adjacent the scrotum during use. It is also typical to provide one or more vibrators in the loop in a position where they would be adjacent a user's partner's clitoris during intercourse.

BRIEF DESCRIPTION OF THE DRAWINGS

Some examples of sexual stimulation devices according to the present teaching will now be described with reference to the accompanying drawings, in which.

DETAILED DESCRIPTION

Figure 1:
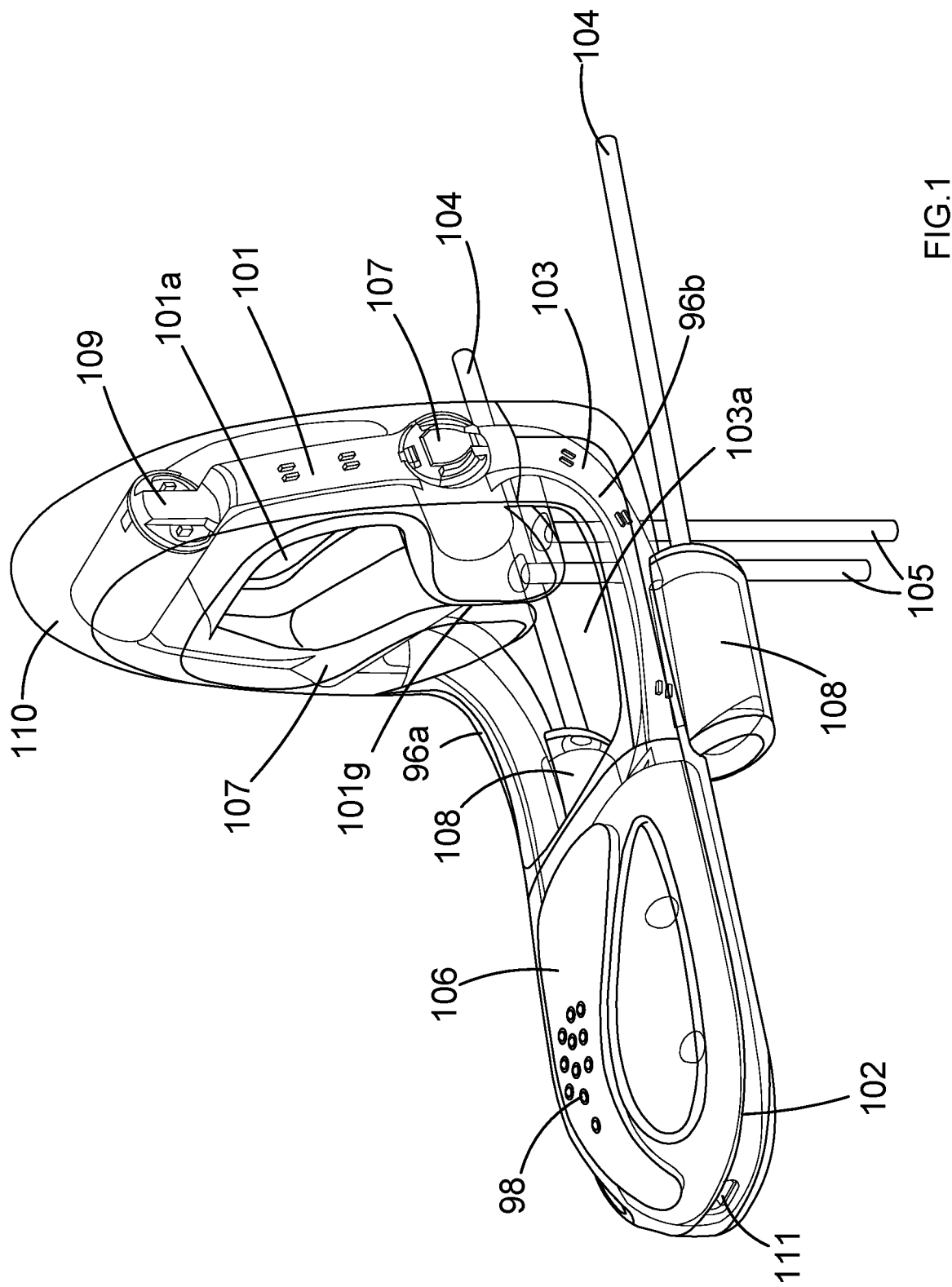
FIG. 1 shows a preferred embodiment of the present teaching having an outer covering, in which the covering has been depicted as translucent so as to indicate the inner workings of the device.
Figure 2:
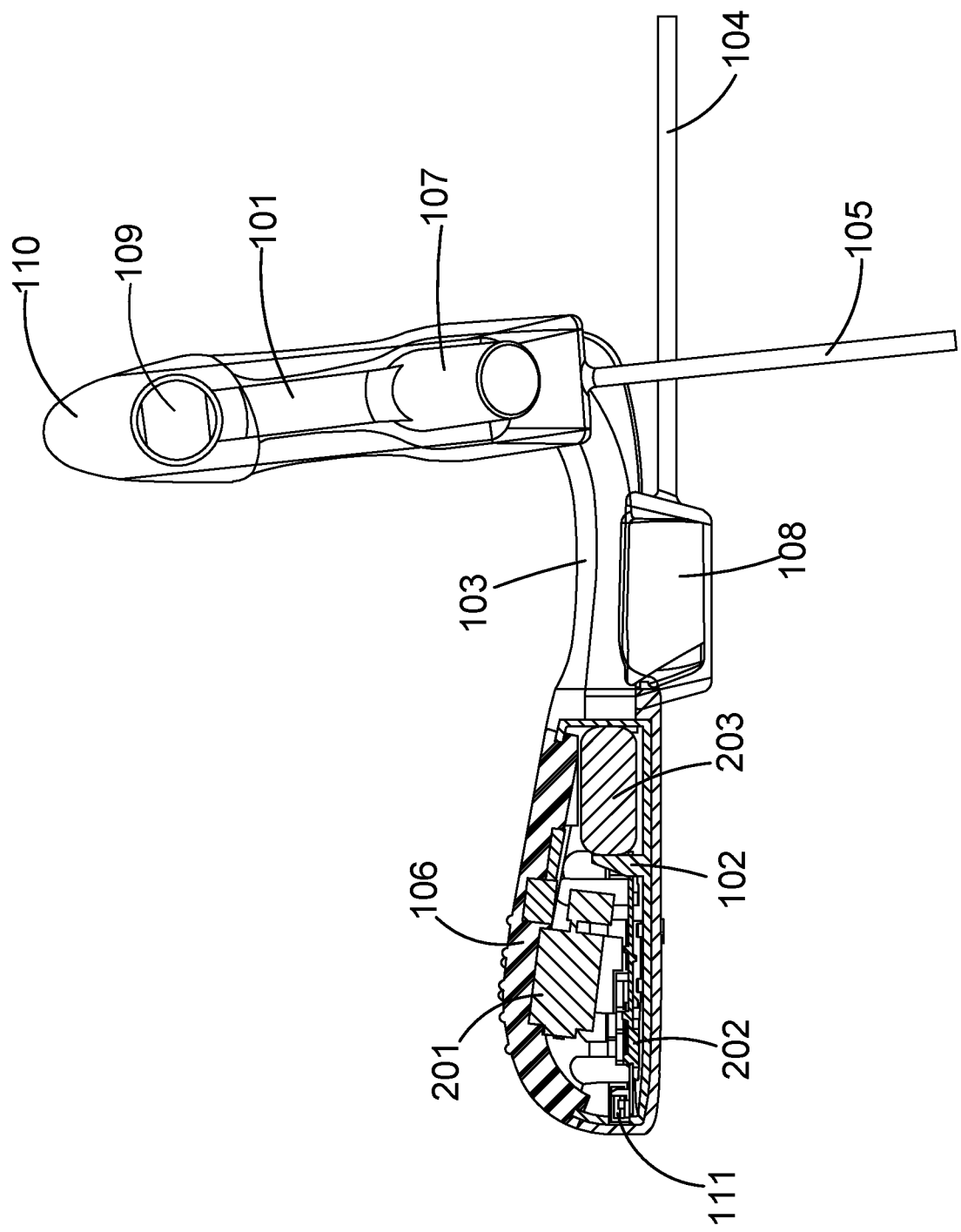
FIG. 2 shows the device of FIG. 1 in profile, including a cross-section of the perineum stimulating portion with the components of the perineum stimulating portion of the device shown in detail.

With reference to FIGS. 1-6, a preferred embodiment of the present teaching comprises an inner structure 301 with an outer covering 110. The inner structure 301 comprises a loop 101, a perineum stimulating portion 102, and a connector 103 extending between the ring 101 and the perineum stimulating portion 102. The inner structure 301 is shown most clearly in FIG. 3.

The loop 101 incorporates a number of features configured to be especially suitable for enhancing and maintaining a user's erection. In particular, the loop 101 includes an aperture 101a through which a user may insert their penis, and a gap 101g in the loop such that the diameter of the loop may be made smaller or larger. The loop 101 comprises a deformable yet resilient material, such that the loop has an equilibrium shape towards which it is biased. The loop 101 may then be made larger to accommodate a user with a larger penis, or to accommodate the growth in a user's penis that accompanies the user achieving an erection. The biasing force towards the equilibrium shape of the loop 101 acts to provide pressure on a user's penis, so as to enhance and maintain a user's erection. The gap 101g in the open loop 101 is also typically configured such that the loop may be made smaller so as to increase the pressure on a user's penis.

Strings 105 can be attached to the respective ends of the open loop 101. A toggle (not shown) can be provided to join the strings together. The toggle can be slid up and down on the strings 105 and can be locked in place. In his way, the toggle and the strings 105 can be used to tighten the loop 101. A user can insert their penis in the gap 101a and then tighten the loop 101 in order to provide the desired level of constriction. Users may have personal preferences in this regard.

The connector 103, which extends between the loop 101 and the perineum stimulating portion 102, is also configured in preferred embodiments to have an equilibrium shape towards which it is biased. The equilibrium shape of this connector 103 is typically as shown in FIG. 1, with a curve that causes the plane of the loop 101 to lie at an acute angle to the plane of the main body of the perineum stimulating portion 102. This acute angle is chosen so that the connector 103 must be flexed away from the equilibrium position in order to be fitted onto a user. This generates a biasing force in the flexible connector 103, urging the perineum stimulating portion 102 into contact with the user's perineum, and urging the loop 101 into contact with the user's body at the base of the penis. In this way the device can be held in tension while being worn so that it can stay in the desired position during intercourse. The flexibility of the connector 103 can allow the device to be worn by a wide variety of users with different body shapes.

The perineum stimulating portion 102 includes an insert 106 having a textured upper surface 98 configured to engage with the user's perineum. The textured surface 98 enhances the gripping action on the perineum caused by the biasing force of the connector 103.

The connector 103 comprises a pair of arms 96a,b with a gap 103a provided in between. The gap 103a is provided with a size suitable for receiving a user's testicles, which can be suspended within the gap 103a. A pair of motors 108 are provided on respective arms 96a,b of the connector 103. The motors 108 are positioned so that they are adjacent the user's testicles, in use. The motors 108 are connected to respective strings 104. A toggle (not shown) can be provided to join the strings 104 together. The toggle can be slid back and forth on the strings 104 and can be locked in place with respect to the strings 104. In his way, the toggle and the strings 104 can be used to deflect the motors 108 inwardly towards one another, to be tightened around a user's testicles, in use. Users may have personal preferences in this regard.

The pair of arms 96a,b extend between the perineum stimulator 102 and the loop 101. The loop 101, which is an open loop, is formed like a pentagon with five sections which need not include straight sides: a clitoral motor housing 109a for a clitoral motor 109; two ventral penis motor housings 107a for ventral penis motors 107; and a pair of connecting arms 94a,b that connect the ventral penis motor housings 107a to the clitoral motor housing 109a. The connecting arms 94a,b are formed of the same material as the arms 96a,b. Therefore, the connecting arms 94a,b are resilient and deformable. The flexibility of these connecting arms 94a,b allows the loop 101 to be expanded and contacted in diameter to fit differently sized penises, and to accommodate the growth of a penis as an erection is established. The flexibility of the connecting arms 94a,b also allows the strings 105 to be used to tighten the loop 101 around the user's penis in use. The resilience of the connecting arms 94a,b means that they can act as a material spring that biases the loop into an equilibrium position.

A number of motors 107, 108, 109 are provided. The ventral penis motors 107 are positioned symmetrically about the loop 101 so that they lie adjacent the underside of a user's penis, in use. The clitoral motor 109 is positioned at the top of the loop 101 at a position that is most distal from the perineum stimulating portion 102. In use, the clitoral motor 109 lies adjacent the clitoris of a user's female partner during intercourse. The testicle motors 108 are positioned so that they lie adjacent the user's testicles, in use. Each of the motors 107, 108, 109 is housed in a respective receiving portion 107a, 108a, 109a in the loop 101 or connector 103. Respective fastening means 107b, 108b, 109b are then used to fasten the motors and maintain them in their respective receiving portion 107a, 108a, 109a. The motors 107, 108, 109, 201 comprise eccentrically mounted weights that cause them to vibrate when the rotor rotates. Other vibrating devices may be used in place of motors, as would occur to the skilled person.

The perineum stimulating portion 102 comprises a hard plastic housing with an outer covering 110 formed of softer material. The hard plastic housing of the perineum stimulating portion 102 is chosen so that it is more rigid than the materials used in the loop 101 and connector 103. By providing a more rigid material in the perineum stimulating portion 102, vibrations of the motors 107, 108, and 109 may be substantially isolated from the perineum stimulating portion 102. This both protects the inner workings of the perineum stimulating portion 102 and localizes the vibrations of motors 107, 108, 109 to improve the efficiency of these motors at providing stimulation to the user and to the user's partner. The relative rigidity of the perineum stimulating portion 102 is usually provided by making the housing of the perineum stimulating portion 102 of a material which has a higher Young's modulus than the material used to construct the inner core of the loop 101 and the connector 103. For example, a low-density polyethylene is typically used for the inner core of the loop 101 and connector 103 while a polycarbonate is used for the housing of the perineum stimulating portion 102. However, it is also possible to design the perineum stimulating portion 102 such that the geometry of its structure confers this increased rigidity, for example by providing supports within the perineum stimulating portion 102.

The outer covering 110 is preferably flexible, deformable and waterproof with silicone being an especially suitable choice of material. Other preferred properties of the outer covering include being waterproof and non-permeable.

A preferred device according to the present teaching includes a rechargeable battery provided within the perineum stimulating portion 102, and a recharging port 111. This port 111 may also be used to connect the sexual stimulation device to a personal computing device. The outer covering 110 has an opening at the position of the port 111. A cover or flap is preferably provided for this opening.

A cavity 92 or through-hole is provided in the housing of the perineum stimulating portion 102. The insert 106 can be received within the cavity 92 and connected to the housing. The insert 106 includes a loop 90 for holding a motor 201. In the embodiment shown, the design of the insert 106 isolates the housing of the perineum stimulating portion 102 from the vibrations of the motor 201. The insert 106 is preferably made of silicon and is connected to the housing of the perineum stimulating portion 102. The interface between the insert 106 and the housing of the perineum stimulating portion 102 is flexible and deformable so that it can absorb vibrations. In this way, vibrations generated by the motor 201 can be substantially localized to the insert 106. The insert 106 can vibrate within the housing of the perineum stimulating portion 102. This can focus vibrations of the motor 201 to the region of the insert 106, which improves the efficiency with which vibrations can be transferred to the perineum.

Figure 4:
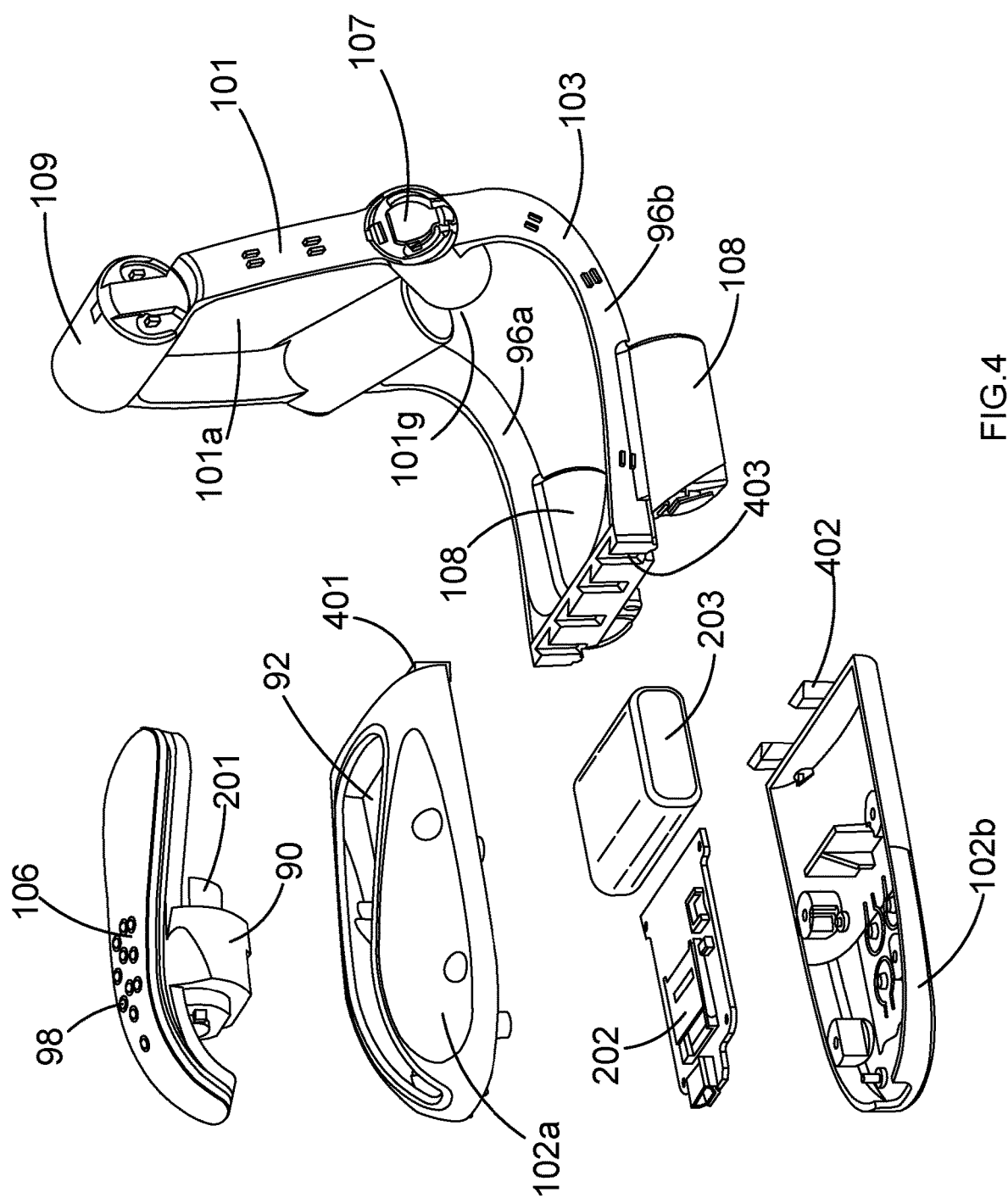
FIG. 4 shows an exploded view of the inner structure of the device of FIGS. 1 to 3.
Figure 5:
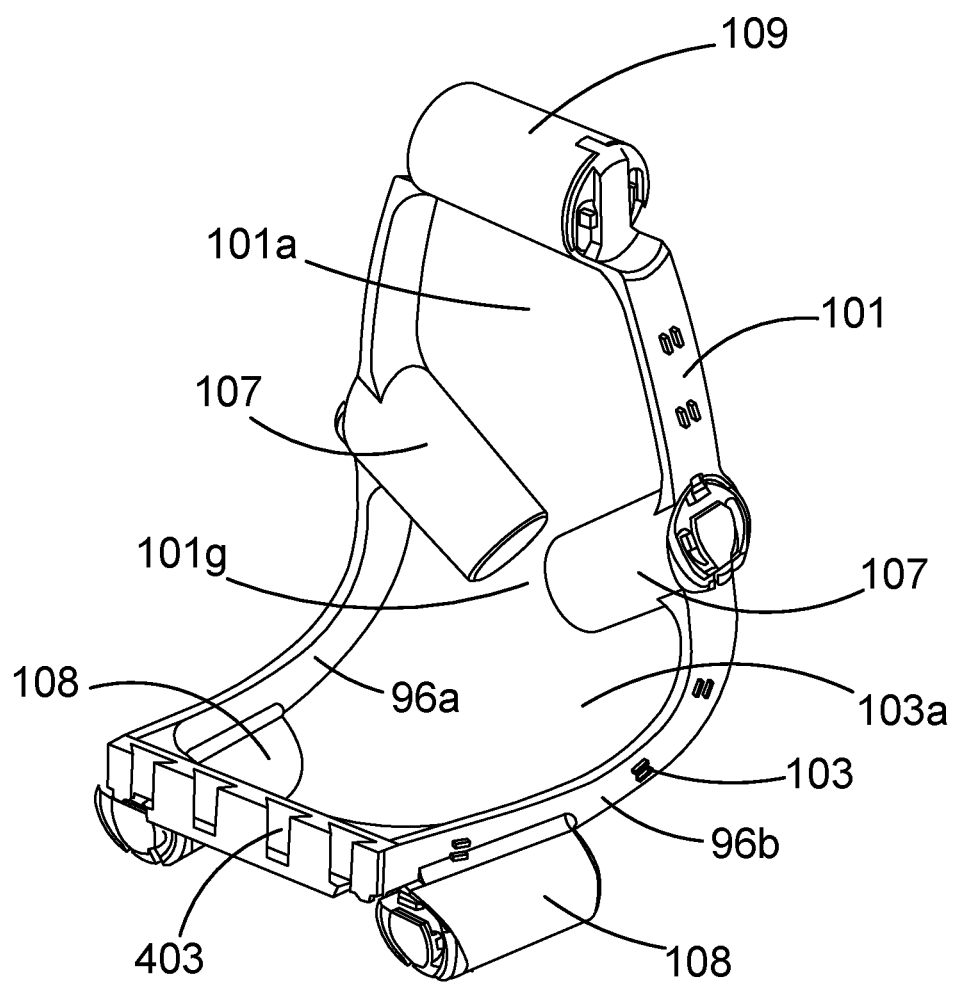
FIG. 5 shows the loop and connector portions of the device of FIGS. 1 to 4, absent the outer covering and the perineum stimulation portion.
Figure 6:
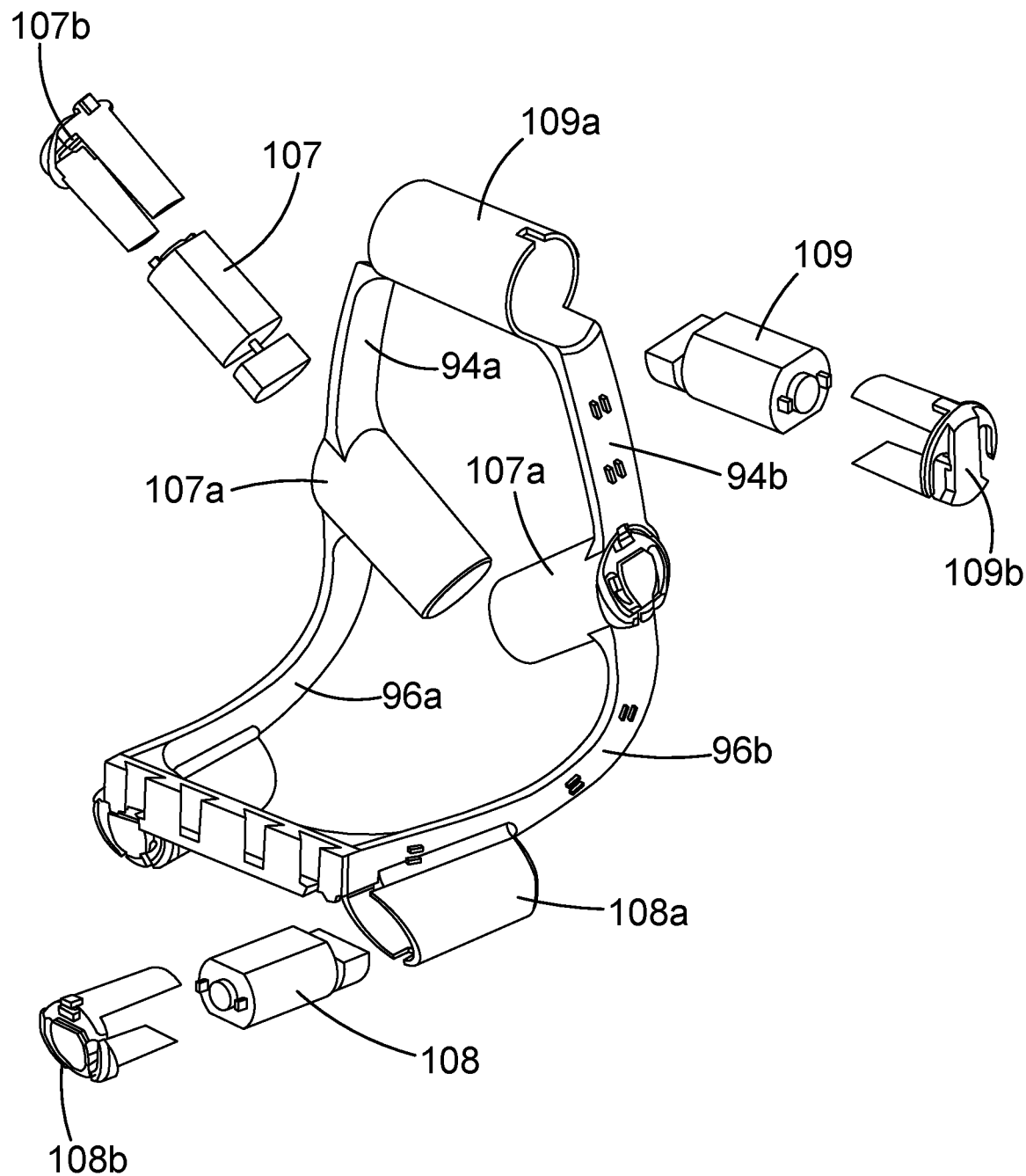
FIG. 6 also shows the loop and connector portions of the device of FIGS. 1 to 4, with the vibrators shown in more detail.

As may be seen in FIG. 4, a battery 203 and a circuit board 202 are situated within the housing of the perineum stimulating portion 102. The perineum stimulating portion 102 comprises an upper housing 102a and a lower housing 102b. One of the reasons that it is desirable for the perineum stimulating portion 102 to be acoustically isolated from the vibrations of the motors 107, 108, 109, and 201 is to prevent damage to the circuit board 202 and battery 203. Vibrational damage has been known to cause weakening in soldered connections, and therefore this helps to improve the robustness of the device. The perineum stimulating portion 102 is an especially suitable location for the circuit board 202 and battery 203 as it may be made with larger dimensions than other portions of the device.

The loop 101 is provided with a profile that is as narrow as possible since this part is provided between sexual partners, in use. The width of the motor 107, 109 is typically the limiting factor in reducing the width of the loop 101.

The battery 203 is preferably rechargeable. The circuit board 202 is arranged for selective control of the motors 107, 108, 109, and 201. The circuit board 202 includes a Bluetooth® transmitter/receiver for connection to a user's mobile phone. The user may then select from vibration patterns either pre-programmed on the circuit board 202 or by using the user's mobile phone to remotely control the motors.

The circuit board 202 is preferably connected to the port 111 to enable interfacing of the sexual stimulation device with a personal computing device. By connecting the port 111 to the circuit board, the user may also control the vibrations of an attachment connected via the port 111.

Figure 3:
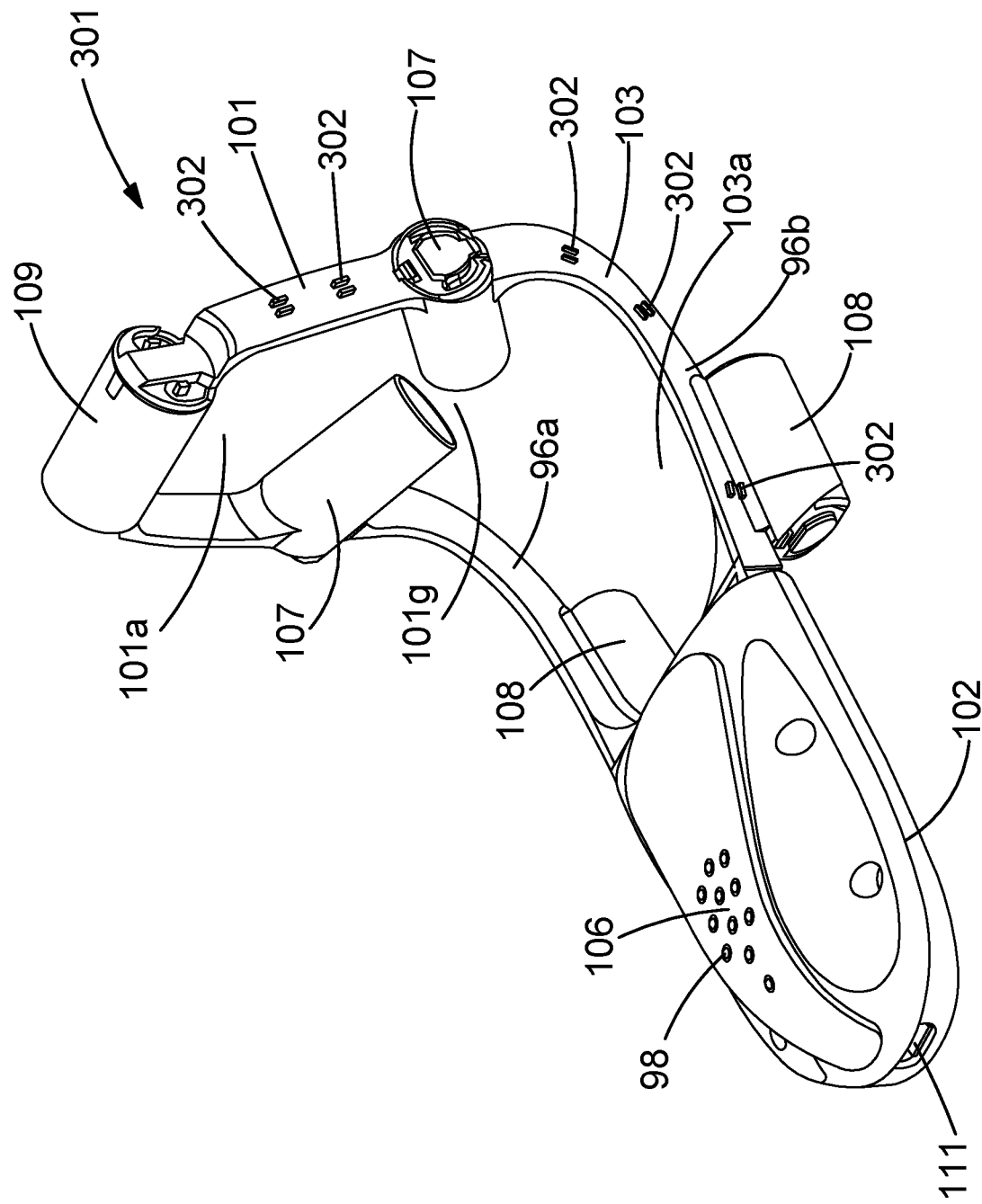
FIG. 3 shows the structure of the device of FIGS. 1 and 2 absent the outer covering.

Not shown in the figures is that the motors of the device are typically connected to the circuit board 202 by wires. These wires could be within the inner structure 301 of the device itself, but are typically provided around the inner structure 301 and within the outer covering 110. Retainers 302 are shown in FIG. 3 provided along the structure 301 which are suitable for receiving wires for connecting the motors 107, 108, and 109 to the circuit board 202. The wires connecting the motor 201 to the circuit board 202 will of course typically be routed within the perineum stimulating portion 102.

As preferred embodiments of the device use a first material for the loop 101 and connector 103 and a different material for the perineum stimulating portion 102, it is typically not possible to manufacture the inner structure 301 as a single unit. Instead the housing of the perineum stimulating portion 102 is formed of an upper part 102a and a lower part 102b which engage with the connector 103 by means of respective connectors 401 and 402 which engage with corresponding indents 403 on the connector. The connectors 401, 402 and indents 403 are configured such that the connector 103 is clamped between the upper and lower parts 102a,b of the housing of the perineum stimulating portion 102, thereby constraining the motion of the connector 103 relative to perineum stimulating portion 102 along all three axes of motion. The upper and lower parts of the housing 102a,b are preferably held together using screws, although other options are available to the person skilled in the art.

The invention claimed is:

1. A sexual stimulation device comprising:
a loop through which a user can insert their penis;
a perineum stimulating portion configured to contact the user's perineum during use; and
a deformable connector extending between the loop and the perineum stimulating portion;
wherein the deformable connector is deformable between a first shape and a second shape;
wherein the deformable connector is biased towards the first shape such that the loop and the perineum stimulating portion are biased towards the user's body during use;
wherein the deformable connector comprises a pair of side arms separated by a gap in which the user's testicles can be received.

2. The sexual stimulation device according to claim 1, wherein a distance between the loop and the perineum stimulating portion is smaller when the deformable connector is in the first shape than when the deformable connector is in the second shape.

3. The sexual stimulation device according to claim 1, wherein the deformable connector comprises a resilient material that is configured to bias the deformable connector towards the first shape.

4. The sexual stimulation device according to claim 1, wherein the perineum stimulating portion is relatively rigid in comparison to the deformable connector.

5. The sexual stimulation device according to claim 1, wherein the loop comprises one or more vibrators adapted to be positioned adjacent the user's partner's clitoris, in use, and configured to stimulate the user's partner's clitoris.

6. The sexual stimulation device according to claim 1, wherein the connector comprises one or more vibrators adapted to be positioned adjacent the user's testicles, in use, and configured to stimulate the user's testicles.

7. A sexual stimulation device comprising:
a loop through which a user can insert their penis, the loop including one or more vibrators;
a perineum stimulating portion including control circuitry; and
a connector extending between the loop and the perineum stimulating portion;
wherein the control circuitry in the perineum stimulating portion is acoustically isolated from vibrations in the loop by means of the connector.

8. A sexual stimulation device comprising:
a loop through which a user can insert their penis;

a perineum stimulating portion including a housing and a cavity in which an insert is provided;
a first vibrator connected to the insert; and
a connector extending between the loop and the perineum stimulating portion;
wherein the housing of the perineum stimulating portion is acoustically isolated from the vibrations of the vibrator by means of the insert.

9. The sexual stimulation device according to claim 8, wherein the insert comprises a first material and the perineum stimulating portion comprises a second material, the second material being more rigid than the first material.

10. The sexual stimulation device according to claim 9, wherein the second material has a larger Young's modulus than the first material.

11. A sexual stimulation device comprising:
an open loop through which a user can insert their penis, the open loop having a first end and a second end and being movable from a first configuration in which the first end is a first distance from the second end to a second configuration in which the first end is a second distance from the second end, the second distance being greater than the first distance;
a perineum stimulating portion configured to contact the user's perineum during use; and
a connector extending between the loop and the perineum stimulating portion;
wherein the loop comprises a resilient inner core configured to bias the loop towards the first configuration;
wherein the loop includes a deformable outer covering.

12. The sexual stimulation device according to claim 11, wherein the open loop is movable from the first configuration to a third configuration in which the first end is a third distance from the second end, the third distance being smaller than the first distance.

13. The sexual stimulation device according to claim 11, wherein the device comprises:
a first string connected to the first end of the open loop;
a second string connected to the second end of the open loop; and
a toggle engaging the first and second strings, whereby the toggle is moveable relative to the first and second strings and can be locked in position relative to the first and second strings in order to urge the open loop towards the third configuration.

14. A sexual stimulation device comprising:
a loop through which a user can insert their penis;
a perineum stimulating portion configured to contact the user's perineum during use; and
a deformable connector extending between the loop and the perineum stimulating portion;
wherein the deformable connector is deformable between a first shape and a second shape;
wherein the deformable connector is biased towards the first shape such that the loop and the perineum stimulating portion are biased towards the user's body during use;
wherein the deformable connector comprises a first material and the perineum stimulating portion includes a second material, the second material being more rigid than the first material.

15. The sexual stimulation device according to claim 14, wherein the loop comprises the first material.

16. The sexual stimulation device according to claim 14, wherein the second material has a larger Young's modulus than the first material.

17. A sexual stimulation device comprising:
a loop through which a user can insert their penis;
a perineum stimulating portion configured to contact the user's perineum during use; and
a deformable connector extending between the loop and the perineum stimulating portion;
wherein the deformable connector is deformable between a first shape and a second shape;
wherein the deformable connector is biased towards the first shape such that the loop and the perineum stimulating portion are biased towards the user's body during use;
wherein the deformable connector is held in a clamp by the perineum stimulating portion.

\* \* \* \* \*